(12) United States Patent
Yesalusky, Jr.

(10) Patent No.: US 7,367,071 B1
(45) Date of Patent: May 6, 2008

(54) PILLOW HAVING WAIST STRAPS/LUMBAR PAIN ALLEVIATION METHOD

(76) Inventor: Edward J. Yesalusky, Jr., 8 Edgehill Rise NW., Calgary, Alberta (CA) T3A 2V4

( * ) Notice: Subject to any disclaimer, the term of this patent is extended or adjusted under 35 U.S.C. 154(b) by 0 days.

(21) Appl. No.: 11/523,294

(22) Filed: Sep. 20, 2006

(51) Int. Cl.
*A47C 16/00* (2006.01)
*A61F 5/37* (2006.01)
(52) U.S. Cl. ............... 5/630; 5/652; 5/657; 128/845
(58) Field of Classification Search ............. 5/630, 5/652, 657; 128/96.1, 845
See application file for complete search history.

(56) References Cited

U.S. PATENT DOCUMENTS

| | | | | |
|---|---|---|---|---|
| 2,521,530 | A * | 9/1950 | McGuffage | 5/630 |
| 4,627,109 | A * | 12/1986 | Carabelli et al. | 2/44 |
| 4,989,591 | A * | 2/1991 | Anders, Jr. | 606/240 |
| 5,048,542 | A * | 9/1991 | Murray | 128/889 |
| 5,199,124 | A * | 4/1993 | Klemis | 5/630 |

\* cited by examiner

*Primary Examiner*—Michael Trettel
(74) *Attorney, Agent, or Firm*—G. F. Gallinger

(57) ABSTRACT

An apparatus for alleviating lower back pain while sleeping on a front side portion of one's body comprising: a pillow cover having a width generally equal to a width of the body, said pillow cover having an elongate opening therealong for insertion of a pillow insert and opposite lateral side straps extending therefrom for encircling the waist of the user; and, a pillow insert having a central portion and similar lateral side portions. A method for alleviating lower back pain while sleeping on a front side portion of one's body comprising the following steps: a) providing a pillow cover having a width generally equal to a width of the body, said pillow cover having an elongate opening therealong for insertion of a pillow insert and opposite lateral side straps extending therefrom for encircling the waist of the user; and, b) positioning a pillow insert having a central portion and similar lateral side portions within the pillow cover; and, c) strapping the pillow cover containing the pillow insert around one's waist positioning said insert on one's front side. When the user the user rolls from on his side onto his front he is supported on the apparatus and thereby the vertebrae in his lower spine are more separated to alleviate spinal cord compression and pain.

16 Claims, 1 Drawing Sheet

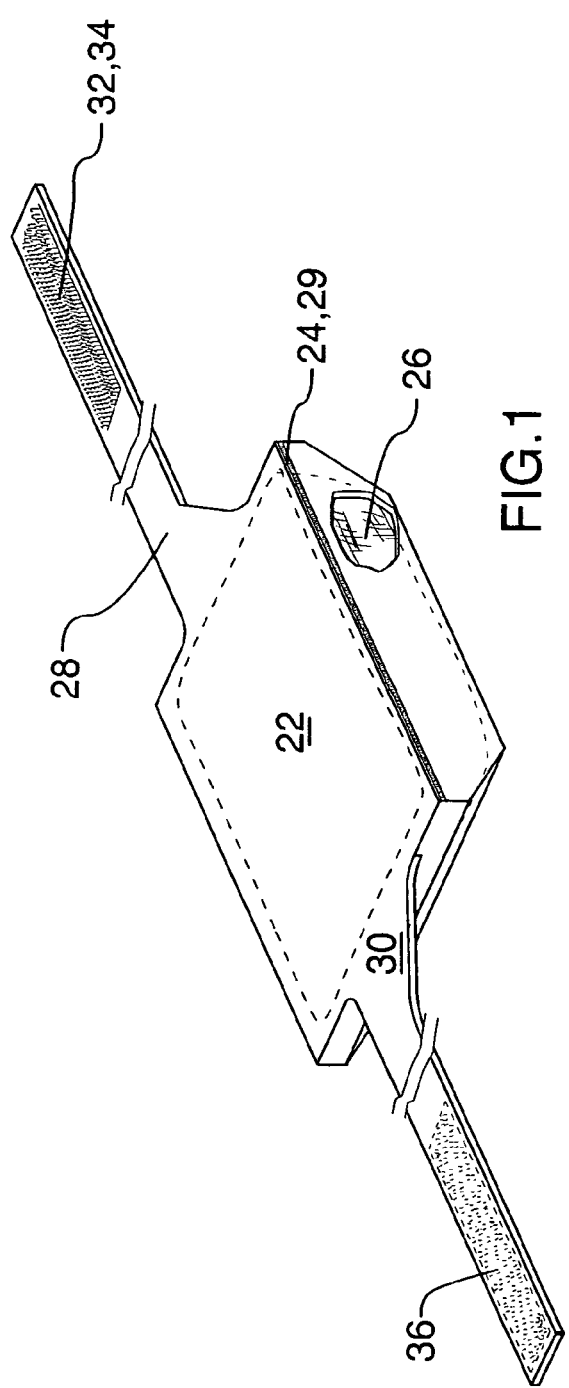
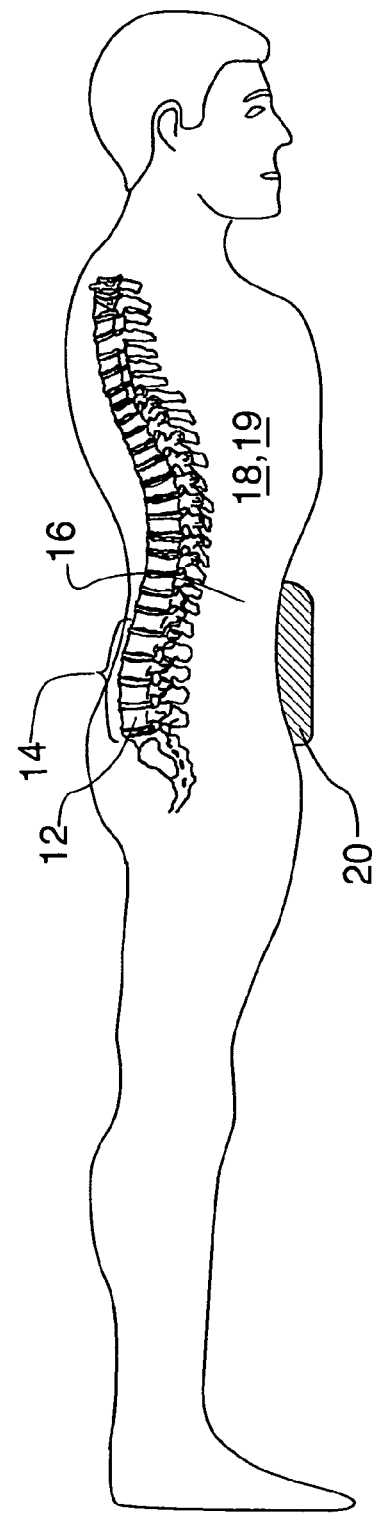

PILLOW HAVING WAIST STRAPS/LUMBAR PAIN ALLEVIATION METHOD

FIELD OF THE INVENTION

This invention relates to paraphernalia for individuals suffering with lower back problems. More particularly this invention relates to a pillow and method of use to alleviate lower back pain. The pillow is strapped about the waist so that it is positioned under their lower stomach while sleeping thereby separating the vertebrae and relieving pressure on the discs in the lower back.

BACKGROUND OF THE INVENTION

The invention herein is disclosed for individuals suffering with lower back pain. The back pain may be caused by bulging discs which press on the spinal chord passing through the vertebrae. Alternatively the back pain may simply be caused by misalignments in the spine so that the vertebrae themselves press on the spinal chord. As individuals age the discs which separate the vertebrae normally shrink. Most individual's typically loose an inch or more of height. The vertebrae in the spine which were once adequately separated and cushioned by the discs therebetween accordingly become closer together. A misalignment between any two vertebrae in the back which may have been nonproblematic in the individual's youth may later in life become a source of chronic pain.

OBJECTS OF THE INVENTION

It is an object of this invention to disclose a cover for a pillow which facilitates maintaining the pillow positioned over the stomach while sleeping. When the pillow is positioned along a front side portion of the body then when the individual lies on their front side the back is gently arched opening the space between the vertebrae so that the spinal chord is not pressed upon, thereby alleviating back pain. It is an object of this invention to disclose a method of alleviating lower back pain. It is yet a further object of this invention to disclose a method of promoting better sleep for individual's which have lower back pain.

One aspect of this invention provides for an apparatus for alleviating lower back pain while sleeping on a front side portion of one's body comprising: a pillow cover having a width generally equal to a width of the body, said pillow cover having an elongate opening therealong for insertion of a pillow insert and opposite lateral side straps extending therefrom for encircling the waist of the user; and, a pillow insert having a central portion and similar lateral side portions. When the apparatus is strapped around and onto the waist of the user the user can then roll from on his side onto his front thereby being supported on the apparatus and thereby having the vertebrae in his lower spine more separated to alleviate spinal cord compression and pain.

A method for alleviating lower back pain while sleeping on a front side portion of one's body comprising the following steps: a) providing a pillow cover having a width generally equal to a width of the body, said pillow cover having an elongate opening therealong for insertion of a pillow insert and opposite lateral side straps extending therefrom for encircling the waist of the user; and, b) positioning a pillow insert having a central portion and similar lateral side portions within the pillow cover; and, c) strapping the pillow cover containing the pillow insert around one's waist positioning said insert on one's front side. When the user the user rolls from on his side onto his front he is supported on the apparatus and thereby the vertebrae in his lower spine are more separated to alleviate spinal cord compression and pain.

Various other objects, advantages and features of this invention will become apparent to those skilled in the art from the following description in conjunction with the accompanying drawings.

FIGURES OF THE INVENTION

FIG. 1 is a perspective view of an apparatus 20 for alleviating lower back pain while sleeping on one's front side.

FIG. 2 is a cross sectional view of an individual sleeping on the apparatus shown in FIG. 1.

The following is a discussion and description of the preferred specific embodiments of this invention, such being made with reference to the drawings, wherein the same reference numerals are used to indicate the same or similar parts and/or structure. It should be noted that such discussion and description is not meant to unduly limit the scope of the invention.

DESCRIPTION OF THE INVENTION

Turning now to the drawings and more particularly to FIG. 1 we have a perspective view of an apparatus 20 for alleviating lower back pain while sleeping on one's front side. FIG. 2 is a cross sectional view of an individual sleeping on the apparatus shown in FIG. 1. Most generally the apparatus 20 for alleviating lower back pain while sleeping on a front side portion of one's body 18 comprises: a) a pillow cover 22 having a width generally equal to a width of the body 18, said pillow cover 22 having an elongate opening 24 therealong for insertion of a pillow insert 26 and opposite lateral side straps 28 extending therefrom for encircling the waist 16 of the user 19; and, b) a pillow insert 26 having a central portion and similar lateral side portions. Then when the apparatus 20 is strapped around and onto the waist 16 of the user 19, the user 19 can then roll from on his side onto his front thereby being supported on the apparatus 20 and thereby having his vertebrae 12 in his lower spine 14 more separated to alleviate spinal cord compression and pain.

Most preferably the cross section of the pillow insert 26 is uniform from a top to a bottom portion thereof, and wherein the lateral side portions of the pillow are sloped so that the pillow insert 26 thickens towards the central portion thereof, so that when the apparatus 20 is strapped to the body 18 the gradual increase in depth facilitates rolling onto a front from a side sleeping position. Most preferably the straps 28 are positioned on a top side portion of the pillow cover 22 so that when the apparatus 20 is strapped on the waist 16 the lower portion thereof extends down the body 18 opposite the lower spine 14.

In the most preferred embodiment of the invention the apparatus 20 further comprises webs 30 which are positioned between the lateral straps 28 and the pillow cover portion of the pillow cover 22 so that when the apparatus 20 is strapped on the user 19 the webs 30 would be positioned adjacent to the sides of the user 19 thereby preventing the bottom portion of the apparatus 20 from bending upwards. In the most preferred embodiment of the invention the pillow insert 26 comprises a resilient foam of the type used in sofa cushions to thereby ensure that the insert 26 maintains its shape during extended use. In one aspect of the invention the density of the foam is selected based on the weight of the user 19 to ensure adequate elevation of the user 19.

The unattached end portions of the straps 28 are provided with hook and loop fasteners 32 for quick and adjustable attachment and removal. Most preferably the inner strap 28 has hooks 34 therealong on an outer side portion thereof and the outer strap has loops therealong an inner portion thereof so that if the straps 28 were misaligned, when attached one on the other, the uncovered hooks 34 would extend outwardly and could not be pressed into the user 19. Most preferably the elongate opening 24 is provided with a zipper 29 to ensure retention and maintenance of the pillow insert 26 in position.

Most generally a method for alleviating lower back pain while sleeping on a front side portion of one's body 18 comprises the following steps: a) providing a pillow cover 22 having a width generally equal to a width of the body 18, said pillow cover 22 having an elongate opening 24 therealong for insertion of a pillow insert 26 and opposite lateral side straps 28 extending therefrom for encircling the waist 16 of the user 19; b) positioning a pillow insert 26 having a central portion and similar lateral side portions within the pillow cover 22; and, c) strapping the pillow cover 22 containing the pillow insert 26 around one's waist 16 positioning said insert 26 on one's front side. Then when the user 19 rolls from on his side onto his front he is supported on the apparatus 20 and thereby the vertebrae 12 in his lower spine 14 are more separated to alleviate spinal cord compression and pain.

This general method can be narrowed by using a more detailed and specified apparatus 20 as detailed above.

While the invention has been described with preferred specific embodiments thereof, it will be understood that this description is intended to illustrate and not to limit the scope of the invention, which is defined by the following claims.

I claim:

1. An apparatus for alleviating lower back pain while sleeping on a front side portion of one's body comprising:
    a pillow cover having a width generally equal to a width of the body, said pillow cover having an elongate opening therealong for insertion of a pillow insert and opposite lateral side straps extending therefrom for encircling the waist of the user; and,
    a pillow insert having a central portion and similar lateral side portions; wherein the cross section of the pillow insert is uniform from a top to a bottom portion thereof, and wherein the lateral side portions of the pillow are sloped so that the pillow insert thickens towards the central portion thereof;
    so that when the pillow is strapped to the body the gradual increase in depth facilitates rolling onto a front from a side sleeping position; and,
    so that when the apparatus is strapped around and onto the waist of the user the user can then roll from on his side onto his front thereby being supported on the apparatus and thereby having the vertebrae in his lower spine more separated to alleviate spinal cord compression and pain.

2. An apparatus as in claim 1 wherein the straps are positioned on a top side portion of thereof so that when the apparatus is strapped on the waist the lower portion extends down the body opposite the lower lumbar spine.

3. An apparatus as in claim 2 further comprising webs are positioned between the straps and the pillow cover portion of the pillow cover so that when the apparatus is strapped on the user the webs would be positioned adjacent to the sides of the user thereby preventing the bottom portion of the apparatus from bending upwards.

4. An apparatus as in claim 1 wherein the pillow insert comprises a resilient foam of the type used in sofa cushions to thereby ensure that the insert maintains its shape during extended use.

5. An apparatus as in claim 4 wherein the density of the foam is selected based on the weight of the user to ensure adequate elevation of the user.

6. An apparatus as in claim 1 wherein unattached end portions of the straps are provided with hook and loop fasteners for quick and adjustable attachment and removal.

7. An apparatus as in claim 6 wherein the inner strap has hooks therealong on an outer side portion thereof and wherein the outer strap has loops therealong an inner portion thereof so that if the straps were misaligned, when attached one on the other, the uncovered hooks would extend outwardly and could not be pressed into the user.

8. An apparatus as in claim 1 wherein the elongate opening is provided with a zipper to ensure retention and maintenance of the pillow insert in position.

9. A method for alleviating lower back pain while sleeping on a front side portion of one's body comprising the following steps:
    a) providing a pillow cover having a width generally equal to a width of the body, said pillow cover having an elongate opening therealong for insertion of a pillow insert and opposite lateral side straps extending therefrom for encircling the waist of the user; and,
    b) positioning a pillow insert having a central portion and similar lateral side portions within the pillow cover; wherein the cross section of the pillow insert is uniform from a top to a bottom portion thereof, and wherein the lateral side portions of the pillow are sloped so that the pillow insert thickens towards the central portion thereof, so that when the pillow is strapped to the body the gradual increase in depth facilitates rolling onto a front from a side sleeping position;
    c) strapping the pillow cover containing the pillow insert around one's waist positioning said insert on one's front side;
    so that when the user the user rolls from on his side onto his front he is supported on the apparatus and thereby the vertebrae in his lower spine are more separated to alleviate spinal cord compression and pain.

10. A method as in claim 9 wherein the straps are positioned on a top side portion of the pillow cover so that when the pillow is strapped on the waist the lower portion of the pillow extends opposite the lower lumbar vertebrae.

11. A method as in claim 10 further comprising webs are positioned between the straps and the pillow cover so that when the apparatus is strapped on the user the webs would be positioned adjacent to the sides of the user thereby preventing the bottom portion of the pillow from bending upwards.

12. A method as in claim 9 wherein the pillow insert comprises a resilient foam of the type used in sofa cushions to thereby ensure that the insert maintains its shape during extended use.

13. A method as in claim 12 wherein the density of the foam is selected based on the weight of the user to ensure adequate elevation of the user.

14. A method as in claim 9 wherein unattached end portions of the straps are provided with hook and loop fasteners for quick and adjustable attachment and removal.

15. A method as in claim 14 wherein the inner strap has hooks therealong an outer side portion and wherein the outer strap has loops therealong an inner portion thereof so that if the straps were misaligned one on the other the uncovered hooks would extend outwardly and could not be pressed into the user.

16. A method as in claim 9 wherein the elongate opening is provided with a zipper to ensure retention and maintenance of pillow insert position.

* * * * *